(12) United States Patent
Kischkat et al.

(10) Patent No.: US 7,601,950 B2
(45) Date of Patent: Oct. 13, 2009

(54) SYSTEM AND METHOD FOR DOWNHOLE OPTICAL ANALYSIS

(75) Inventors: Tobias Kischkat, Niedersachsen (DE);
Stefen Sroka, Niedersachsen (DE);
Peter Schaefer, GroB Kreutz (DE)

(73) Assignee: Baker Hughes Incorporated, Houston, TX (US)

( * ) Notice: Subject to any disclaimer, the term of this patent is extended or adjusted under 35 U.S.C. 154(b) by 74 days.

(21) Appl. No.: 11/860,821

(22) Filed: Sep. 25, 2007

(65) Prior Publication Data
US 2009/0078860 A1    Mar. 26, 2009

(51) Int. Cl.
*G01V 5/08*    (2006.01)
(52) U.S. Cl. .................................. 250/269.1
(58) Field of Classification Search ............... 250/269.1
See application file for complete search history.

(56) References Cited

U.S. PATENT DOCUMENTS

| | | | |
|---|---|---|---|
| 4,791,446 A | 12/1988 | Ishida et al. | |
| 4,994,671 A | 2/1991 | Safinya | |
| 5,305,233 A | 4/1994 | Kawagoe et al. | |
| 5,912,463 A | 6/1999 | Mizuno et al. | |
| 6,087,656 A | 7/2000 | Kimmich | |
| 6,150,649 A | 11/2000 | Wake et al. | |
| 6,175,383 B1 | 1/2001 | Yadid-Pecht | |
| 6,649,416 B1 | 11/2003 | Kauer et al. | |
| 6,823,298 B1 | 11/2004 | Jones et al. | |
| 7,196,786 B2 | 3/2007 | DiFoggio | |
| 2001/0053556 A1* | 12/2001 | Anderson et al. | 436/518 |
| 2003/0056581 A1 | 3/2003 | Turner et al. | |

FOREIGN PATENT DOCUMENTS

| | | |
|---|---|---|
| EP | 0 562 976 A1 | 9/1993 |
| WO | WO 2007/067743 A2 | 6/2007 |

* cited by examiner

*Primary Examiner*—David P Porta
*Assistant Examiner*—Kiho Kim
(74) *Attorney, Agent, or Firm*—G. Michael Roebuck

(57) ABSTRACT

A method for measuring optical properties of a fluid downhole, the method comprising measuring intensity of light interacting with the fluid downhole for each of one or more wavelengths; integrating each intensity of light for each wavelength for an integration time; and estimating the optical property from a difference between a starting value and an ending value for the integral of the intensity of light over time divided by the integration time for the wavelength. An apparatus is disclosed for measuring an optical property of a fluid downhole, the apparatus comprising one or more photodiodes that measure an intensity of light interacting with the fluid downhole for each of one or more wavelengths; and one or more integration circuits that each integrates an intensity of light for one wavelength for an integration time.

26 Claims, 8 Drawing Sheets

SYSTEM AND METHOD FOR DOWNHOLE OPTICAL ANALYSIS

BACKGROUND

1. Field of the Invention

The present disclosure relates to the field of downhole optical analysis.

2. Background

In the oil and gas industry, formation testing tools have been used for monitoring formation pressures along a wellbore, for obtaining formation fluid samples from the wellbore and predicting performance of reservoirs around the wellbore. Such formation testing tools typically contain an elongated body having an elastomeric packer that is sealingly urged against a zone of interest in the wellbore to collect formation fluid samples in storage chambers placed in the tool. During drilling of a wellbore, a drilling fluid ("mud") is used to facilitate the drilling process and to maintain a pressure in the wellbore greater than the fluid pressure in the formation(s) surrounding the wellbore. This is particularly useful when drilling into formations where the pressure is abnormally high.

The formation testing tools retrieve formation fluids from the desired formations or zones of interest, test the retrieved fluids to ensure that the retrieved fluid is substantially free of mud filtrates, and collect such fluids in one or more chambers associated with the tool. The collected fluids are brought to the surface and analyzed to determine properties of such fluids and to determine the condition of the zones or formations from where such fluids have been collected.

SUMMARY

A method is disclosed for estimating optical properties of a fluid downhole, the method comprising measuring intensity of light interacting with the fluid downhole for each of one or more wavelengths; integrating the measured intensity of light for each wavelength for one of one or more integration times; and estimating the optical property for each wavelength from a difference between a starting value and an ending value for the integral of the intensity of light for each wavelength divided by the integration time for each wavelength. An apparatus for estimating an optical property of a fluid downhole is disclosed, the apparatus comprising one or more photodiodes that measure an intensity of light interacting with the fluid downhole for each of one or more wavelengths; and one or more integration circuits that each integrate the measured intensity of light for one wavelength for one of one or more integration times.

DETAILED DESCRIPTION OF ILLUSTRATIVE EMBODIMENTS

Figure 1:
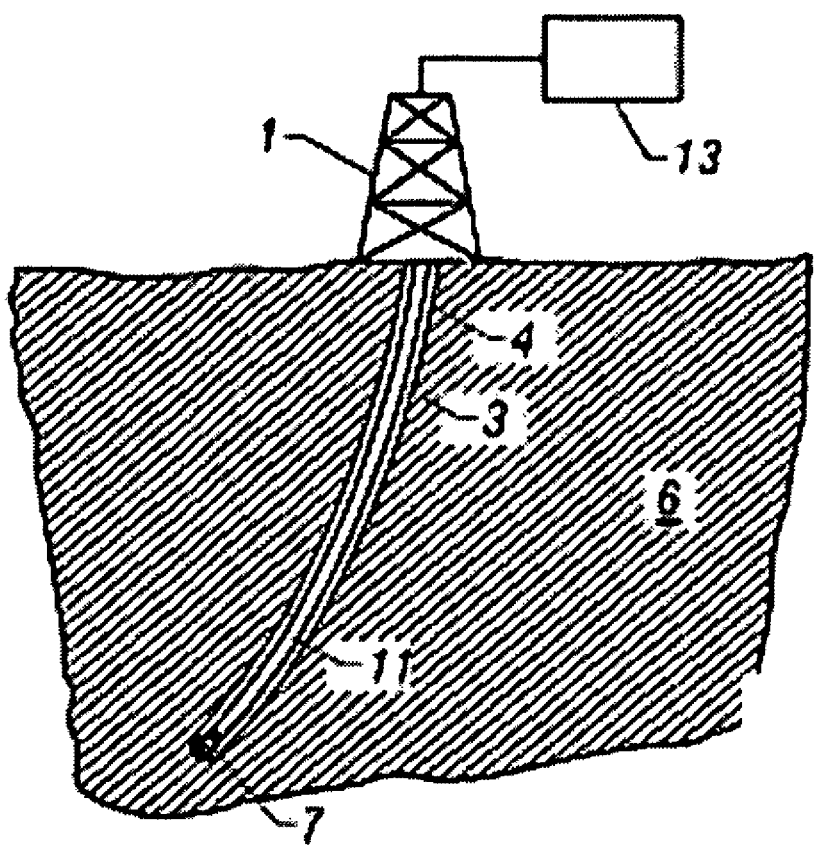
FIG. 1 is a schematic depiction of a particular illustrative embodiment in a monitoring while drilling environment.

In another illustrative embodiment a downhole optical measurement apparatus is provided including an integration circuit for optical fluid analysis. In another embodiment the apparatus is an integrating spectrometer. In another embodiment the apparatus further includes one or more light sources, a measurement chamber (where the formation or other downhole fluid flows between optical windows), a monochromatic filtering device and one or more light detectors. In another embodiment for fluorescence spectra measurements the fluid is illuminated by ultraviolet light and the fluorescence light emitted by the fluid at longer wavelengths than the excitation wavelength is detected by one or more light detectors. In another embodiment discrete photodiodes are used as light detectors. In another embodiment an integration circuit in combination with a photo diode delivers the integrated summation of a photo diode's current over a predetermined dynamically adjusted integration time. The average photo current is obtained by dividing the resulting integrated intensity value by the integration time. For purposes of this disclosure and the claims the term "comprises" and "comprising" mean "including but not limited to".

In another illustrative embodiment, an integration circuit or function is provided that reduces noise effects on the photodiode output caused by light source instability or an inhomogeneous fluid in the measurement chamber. Light source instability can be caused by extreme temperatures down hole and aging of the light source and photodiode circuitry. As the temperature increases downhole the output of the light source can vary and the photodiode current output diminished. The light source and photodiode signal output are also subject to electrical noise or disturbances in the power supplied to the light source and the photodiodes. These electrical power disturbances can cause the output of the light source and the output of the photodiodes to vary. Additionally the photo diode itself generates increasing noise with increasing temperature. In addition, inhomogeneous fluids containing fluids, gas bubbles and solids may cause intermittent optical intensity peaks and valleys which can briefly skew an optical intensity reading while a gas bubble or solid pass intercept a light beam passing through a fluid cell that otherwise contains substantially fluid. In this disclosure, the term fluid is used to include both gas and fluid, as a fluid can also be a gas, supercritical gas or a mixture of gas and fluid.

In another illustrative embodiment, the integration function and integration circuit processes the photodiodes' output currents to widen the dynamic range of the photodiodes' output signal. The output signal gain is proportional to the integration time. In another illustrative embodiment, the integration time is dynamically and interactively adjusted on a periodic basis consistent with a shortest integration time for a particular photodiode for a particular wavelength. In another illustrative embodiment, the integration time for each wavelength or photodiode is dynamically and interactively adjusted based on noise, temperature and cumulative integrated intensity or current levels indicative of light intensity in a particular wavelength.

In another particular embodiment a method is disclosed for estimating optical properties of a fluid downhole, the method comprising measuring intensity of light interacting with the fluid downhole for each of one or more wavelengths; integrating the measured intensity of light for each wavelength for one of one or more integration times; and estimating the optical property for each wavelength from a difference between a starting value and an ending value for the integral of the intensity of light for each wavelength divided by the integration time for each wavelength. In another particular embodiment of the method the intensity of light for each of the plurality of wavelengths is measured using a discrete photodiode, the method further comprising adjusting the integration time for each wavelength based on an initial intensity of light for each wavelength.

In another particular embodiment of the method API gravity is estimated from a historical API gravity. In certain formation or geographic regions, prior wells yield historical data on expected API levels. Thus, in some cases the API level can be estimated and stored as historical API level data in a computer readable medium accessible to a processor in the downhole tool. In another particular embodiment of the method, the method further comprises regularly integrating dark current for each detector; and subtracting the dark value from the corresponding intensity of light measurement for each wavelength. In another particular embodiment of the method the optical property is a spectrum of light selected from the group consisting of fluorescence, absorbance (the reciprocal of transmittance) and reflectance. In another particular embodiment of the method the fluid is a gas, supercritical gas or a mixture of gas and fluid.

In another particular embodiment of the method, the method further comprises sampling each intensity of light measurement for noise at a noise sampling rate, wherein the noise sampling rate is faster than sampling rate for the integrated measured intensity of light; and smoothing noise in the integrated intensity of light measurement. In another particular embodiment of the method the noise is caused by a source selected from the group consisting of light source instability or an inhomogeneous fluid in the measurement chamber or fluid passage. In another particular embodiment of the method the method further comprises measuring duration of the noise in the intensity of light measurement; extending the integration time for each wavelength based on the duration of the noise; and eliminating a measurement for a wavelength when the duration of the noise for the wavelength is longer than the integration time for the wavelength. In another particular embodiment of the method, the method further comprises ending the integration time when the integrated measured intensity of light for the wavelength has reached a value selected from the group consisting of a percentage of an analog to digital converter range and a voltage rating for an integrating capacitor.

In another particular embodiment an apparatus for estimating an optical property of a fluid downhole is disclosed, the apparatus comprising one or more photodiodes that measure an intensity of light interacting with the fluid downhole for each of one or more wavelengths; and one or more integration circuits that each integrate the measured intensity of light for each wavelength for one of a plurality of integration times. In another particular embodiment of the apparatus the apparatus further comprises a processor that estimates the optical property for each wavelength from a difference between a starting value and an ending value at the end of the integration time for the integration of the measured intensity of light for each wavelength divided by the integration time for each wavelength. In another particular embodiment the apparatus further comprises one or more discrete photo detectors, wherein the intensity of light for each wavelength is measured with one of the plurality of discrete photo detectors; and an integration time controller that adjusts each integration time for each wavelength based on the intensity of light for the wavelength. The term wavelength is used herein to describe a center wavelength for a filter that passes substantially all light at a given wavelength and substantially attenuates light at all other wavelengths.

In another particular embodiment of the apparatus the integration time control further comprises an initial integration time value for each wavelength or frequency band based on a parameter selected from the group consisting of API gravity for the fluid, initial intensity of light for the frequency band and downhole temperature. In another particular embodiment of the apparatus API gravity for the fluid is estimated from a historical API gravity data stored in a computer readable medium. In another particular embodiment the apparatus the apparatus further comprises a light input control that substantially eliminates light entering the photo detectors for measuring integrated dark signal intensity for each photo detector to subtract the integrated dark signal intensity from the initial intensity measurement for the photo detectors. In another particular embodiment of the apparatus the optical property is a spectrum of light selected from the group consisting of fluorescence, absorbance, and reflectance. In another particular embodiment an apparatus the fluid is a gas.

In another particular embodiment of the apparatus, the apparatus samples intensity of light measurement for noise at a noise sampling rate, wherein the noise sampling rate is faster than a sampling rate for the integrated measured intensity of light and smoothes noise in the intensity measurement or integrated output of the photodiode. In another particular embodiment of the apparatus the noise is caused by a source selected from the group consisting of light source instability or an inhomogeneous fluid in the measurement chamber. In another particular embodiment of the apparatus, the apparatus further comprises a circuit that measures a duration of noise in the light intensity measurement; and a circuit that extends the integration time for at least one wavelength based on the duration of the noise and eliminates a measurement in a wavelength if the duration of noise is longer than the integration time for the wavelength. In another illustrative embodiment the circuit that measures the duration of noise is processor. In another illustrative embodiment the circuit ends the integration time for a wavelength when the integrated measured intensity of light for the wavelength has reached a value selected from the group consisting of a predetermined percentage of an analog to digital converter range and a voltage rating for an integrating capacitor. In another particular embodiment of the apparatus the integration circuit extends a dynamic range for the intensity of light measurements by using a dynamically adjusted integration time.

Another illustrative embodiment provides an adaptive system (e.g., using a closed loop controller) to adjust the integration time to a dynamically adjusted value for each separate photodiode. The integrated photodiode output measurement is performed differentially. The output signal of the integration circuit or function receiving the photodiode current is measured at a start of the integration time and at the end of the integration time. A difference between the integrated photo current start and end values, divided by the integration time is used as a measurement result for the photodiode. This differential measurement result substantially reduces reset errors as the measurement value after applying the reset signal is not exactly zero.

A dark measurement or a measurement signal with the light source turned off or blocked light input to the detector is performed periodically to measure the intensity of a dark signal for each wavelength, that is, the level of photodiode current when there is no light being received by the photodiode. The integration time for dark measurement is substantially the same as the integration time chosen for light measurement at the wavelength. The dark signal intensity is used as a calibration value and subtracted from the light signals for each wavelength to reduce the error caused by the photodiodes dark current signal for each wavelength to be measured. In another embodiment, a differential measurement and dark signal calibration are used in downhole fluorescence detectors.

In another illustrative embodiment, an apparatus is provided in which visible, fluorescent, mid infrared and near infrared (IR) analysis of the fluids is performed. In another embodiment the analysis is performed in the borehole, without having to transport recovered samples of the fluid to the surface for chemical analysis. The infrared portion part of the electromagnetic spectrum of a substance contains absorption features due to the molecular vibrations of the constituent molecules. The absorptions arise from both fundamentals and combination bands and overtones (multiple quanta transitions occurring in the mid- and the near-infrared region from 0.8-2.5 microns). The position (frequency or wavelength) of these absorptions contain information as to the types of molecular structures that are present in the material, and the intensity of the absorptions contains information about the amounts of the molecular types that are present. To use the information in the spectra for the purpose of identifying and quantifying either components or properties a calibration is performed to establish the relationship between the absorbance and the component or property that is to be estimated.

For complex mixtures, where considerable overlap between the absorptions of individual constituents occurs, such calibrations can be accomplished using various chemometric data analysis methods. In complex mixtures, each constituent generally gives rise to multiple absorption features corresponding to different vibrational motions. The intensities of these absorptions vary together in a linear fashion as the concentration of the constituent varies. Such features are said to have intensities which are correlated in the frequency (or wavelength) domain. This correlation allows these absorptions to be mathematically distinguished from random spectral measurement noise which show less or no such correlation. The linear algebra computations which separate the correlated absorbance signals from the spectral noise form the basis for techniques such as Principal Components Regression (PCR) and Partial Least Squares (PLS). PCR is essentially the analytical mathematical procedure of Principal Components Analysis (PCA), followed by regression analysis. PCR and PLS are used to estimate elemental and chemical compositions and to a lesser extent physical or thermodynamic properties of solids, liquids and gases based on their mid- or near-infrared spectra.

These chemometric methods include but are not limited to the collection of mid- or near-infrared spectra of a set of representative samples; mathematical treatment of the spectral data to extract the Principal Components or latent variables (e.g. the correlated absorbance signals described above); and regression of these spectral variables against composition and/or property data to build a multivariate model. The analysis of new samples then involves the collection of their spectra, the decomposition of the spectra in terms of the spectral variables, and the application of the regression equation to calculate the composition/properties.

In another embodiment visible and near and mid IR region light is passed through the fluid sample. A spectrometer measures the spectrum of the transmitted and the back scattered or reflected light, and knowing the spectrum of the incident light, transmission and backscattered absorption spectra for the sample are determined. Using absorption spectra of water, gas, crude and refined oils, and drilling fluids, a least squares analysis is performed that models the observed spectra as a weighted sum of the spectra of its components, the least squares analysis giving the composition of the fluid in terms of weights of the various components. In another embodiment an ultraviolet source excites fluorescence in the fluid sample. The fluorescent light is back scattered and measured by one or more light detectors to determine the amount of fluorescence and/or fluorescence spectrum.

Turning now to FIG. 1, a drilling operation according one particular illustrative embodiment is shown in FIG. 1. A drilling rig 1 drives a drill string 3 that, which typically is comprised of a number of interconnecting sections. A downhole assembly 11 is formed at the distal end of the drill string 3. The downhole assembly 11 includes a drill bit 7 that advances to form a bore 4 in the surrounding formation 6. A portion of the downhole assembly 11, incorporating an electronic system 8 and cooling systems according to a particular illustrative embodiment is shown in FIG. 2.

Figure 2:
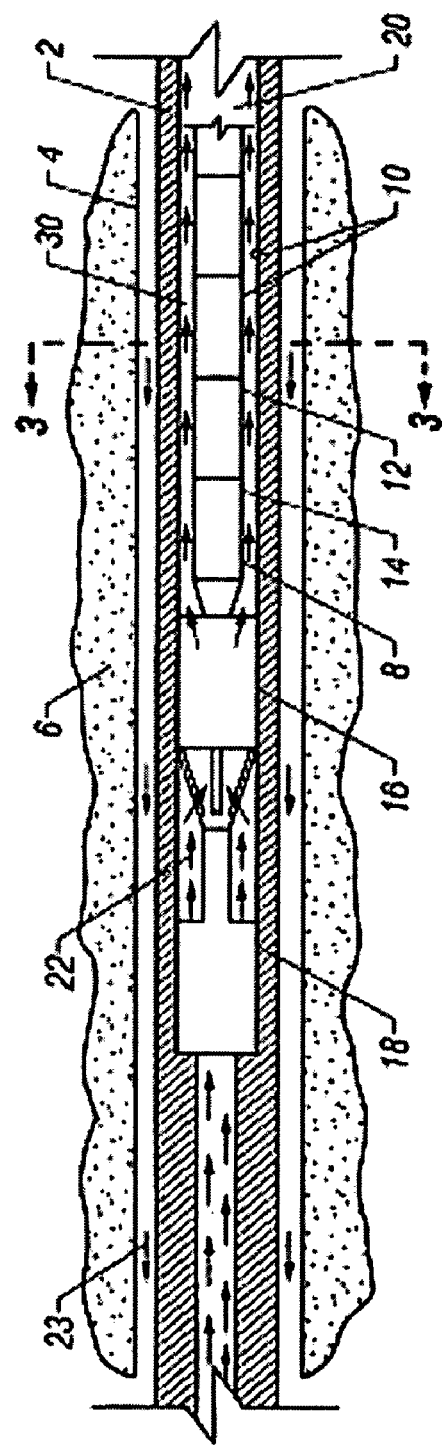
FIG. 2 is a longitudinal cross section through a portion of a downhole tool attached to the drill string as shown in FIG. 1 incorporating an optical sensor.

Turning now to FIG. 2, the electrical system 8 may, for example, provide information to a data acquisition and analysis system 13 located at the surface. Analysis may also be performed downhole. The electrical system 8 includes one or more electronic components. Such electronic components include those that incorporate transistors, integrated circuits, resistors, capacitors, and inductors, as well as electronic components such as sensing elements, including accelerometers, magnetometers, photomultiplier tubes, and strain gages.

The downhole portion 11 of the drill string 3 includes a drill pipe, or collar, 2 that extends through the bore 4. As is conventional, a centrally disposed passage 20 is formed within the drill pipe 2 and allows drilling mud 22 to be pumped from the surface down to the drill bit. After exiting the drill bit, the drilling mud 23 flows up through the annular passage formed between the outer surface of the drill pipe 2 and the internal diameter of the bore 4 for return to the surface. Thus, the drilling mud flows over both the inside and outside surfaces of the drill pipe. Depending on the drilling operation, the pressure of the drilling mud 22 flowing through the drill pipe internal passage 20 will typically be between 1,000 and 20,000 pounds per square inch, and, during drilling, its flow rate and velocity will typically be in the 100 to 1500 GPM range and 5 to 150 feet per second range, respectively.

As also shown in FIG. 2, the electrical system 8 is disposed within the drill pipe central passage 20. The electrical system 8 includes a number of sensor modules 10, a control module 12, a power regulator module 14, an acoustic pulser module 18, and a turbine alternator 16 that are supported within the passage 20, for example, by struts extending between the modules and the drill pipe 2. According to the current disclosure, power for the electrical system 8, including the electronic components and sensors, discussed below, is supplied by a battery, a wire line or any other typical power supply method such as the turbine alternator 16, shown in FIG. 2, which is driven by the drilling mud 22. The turbine alternator 16 may be of the axial, radial or mixed flow type. Alternatively, the alternator 16 could be driven by a positive displacement motor driven by the drilling mud 22, such as a Moineau-type motor. In other embodiments, power could be supplied by any power supply apparatus including an energy storage device located downhole, such as a battery.

Figure 3:
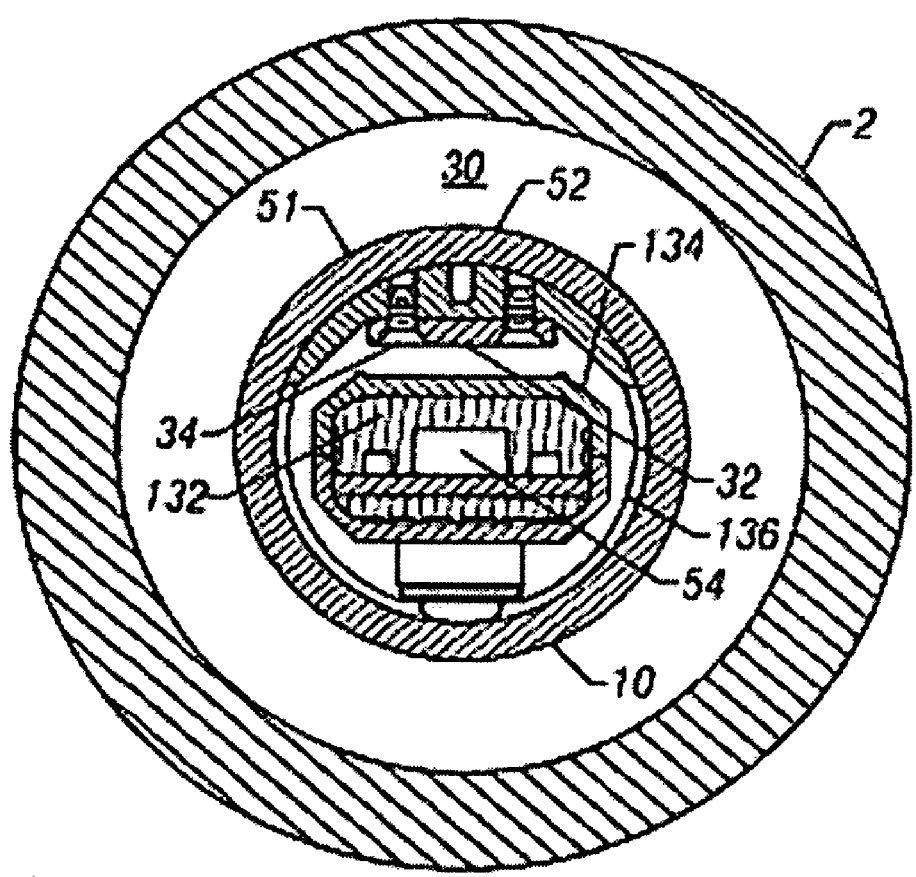
FIG. 3 is a transverse cross section through one of the sensor modules shown in FIG. 2 taken along line III-III.

As shown in FIG. 3, each sensor module 10 is comprised of a cylindrical housing 52, which in an illustrative embodiment is formed from stainless steel or a beryllium copper alloy. An annular passage 30 is formed between the outer surface 51 of the cylindrical housing 52 and the inner surface of the drill pipe 2. The drilling mud 22 flows through the annular passage 30 on its way to the drill bit 7, as previously discussed. In another particular embodiment, formation fluid enters the annular passage for optical analysis. The housing 52 contains an electronic component 54 for the sensor module. The electronic component 54 may, but according to a particular illustrative embodiment, does not necessarily, include one or more printed circuit boards including a processor associated with the sensing device, as previously discussed. Alternatively, the assembly shown in FIG. 3 comprises the control module 12, power regulator module 14, or pulser module 18, in which case the electronic component 54 may be different than those used in the sensor modules 10, although it may, but does not necessarily, include one or more printed circuit boards. According to a particular illustrative embodiment, one or more of the electronic components or sensors in the electrical system 8 are cooled by evaporation of liquid from the liquid supply 132 adjacent to or surrounding electronics 54.

Figure 4:
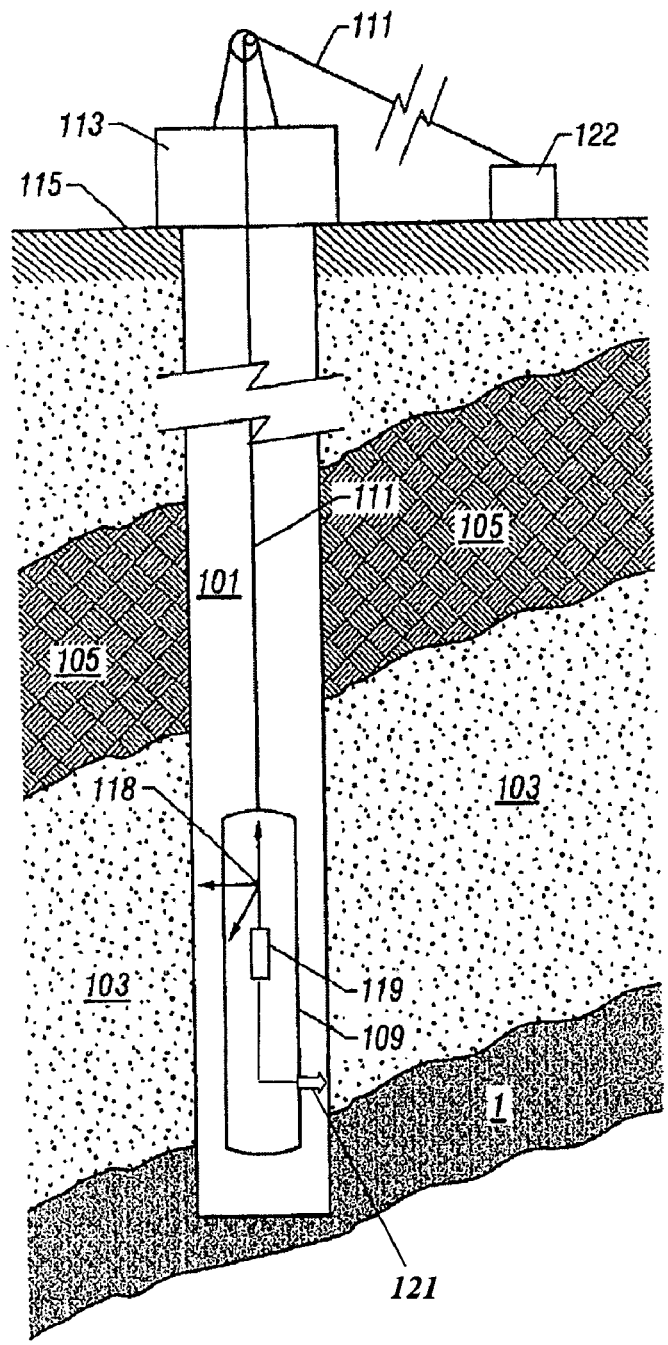
FIG. 4 is a schematic depiction of an illustrative embodiment shown deployed in a wire line environment.

Turning now to FIG. 4 a wire line deployment of an embodiment is depicted. FIG. 4 schematically depicts a well bore 101 extending into a laminated earth formation, into which well bore a logging tool including sensors and electronics as used according to the present invention has been lowered. The well bore in FIG. 4 extends into an earth formation which includes a hydrocarbon-bearing sand layer 103 located between an upper shale layer 105 and a higher conductivity than the hydrocarbon bearing sand layer (formation) 103. An electronic logging tool 109 having sensors and electronics and a sorption or thermal conductive cooling system, has been lowered into the well bore 101 via a wire line 111 extending through a blowout preventer 113 (shown schematically) located at the earth surface 115. The surface equipment 122 includes an electric power supply to provide electric power to the set of coils 118 and a signal processor to receive and process electric signals from the sensors and electronics 119. A port 121 provides fluid communication between the electronics and sensor 109 and the formation 103. The electronics and sensor include but are not limited to a processor, photodiodes and an integration circuit as described below with respect to FIGS. 5-8. Alternatively, a power supply and signal processor are located in the logging tool. In the case of the wire line deployment, the wire line may be utilized for provision of power and data transmission.

Figure 5:
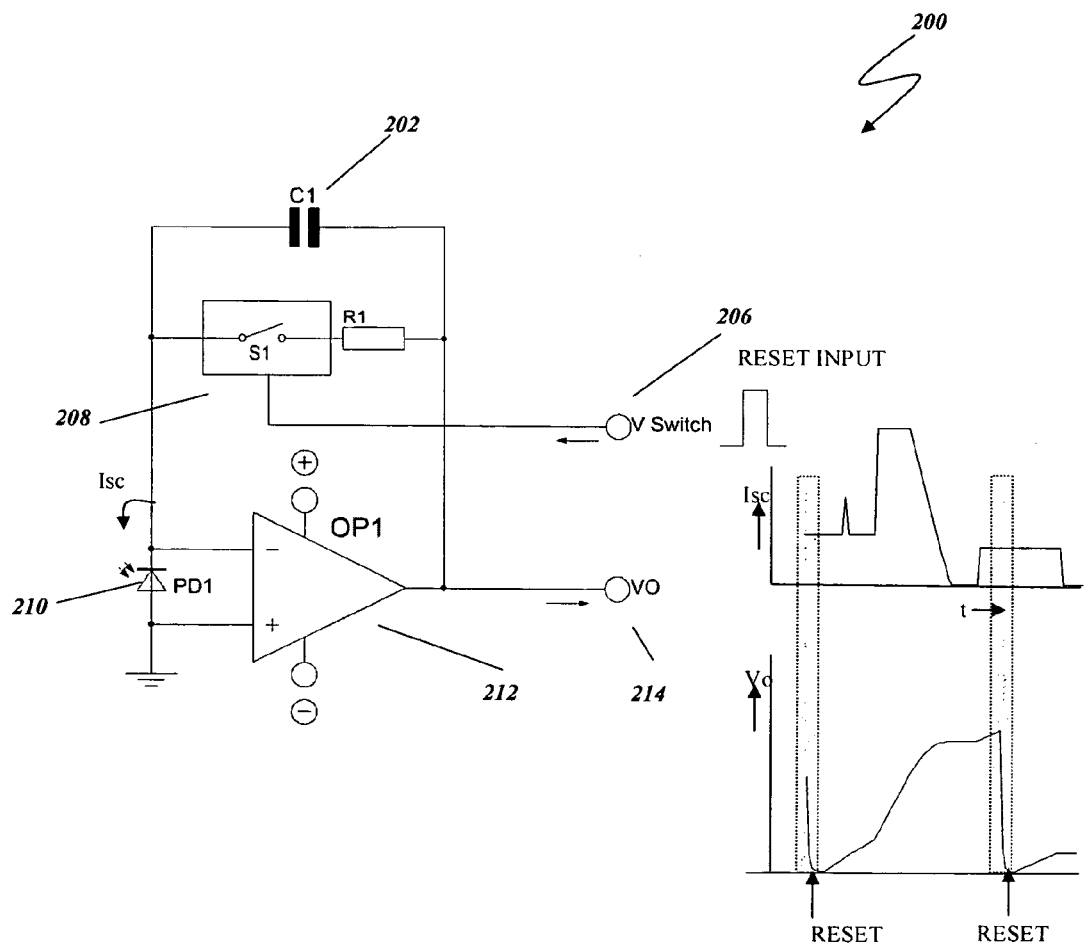
FIG. 5 is a schematic diagram of an integration circuit provided in another illustrative embodiment.
Figure 6:
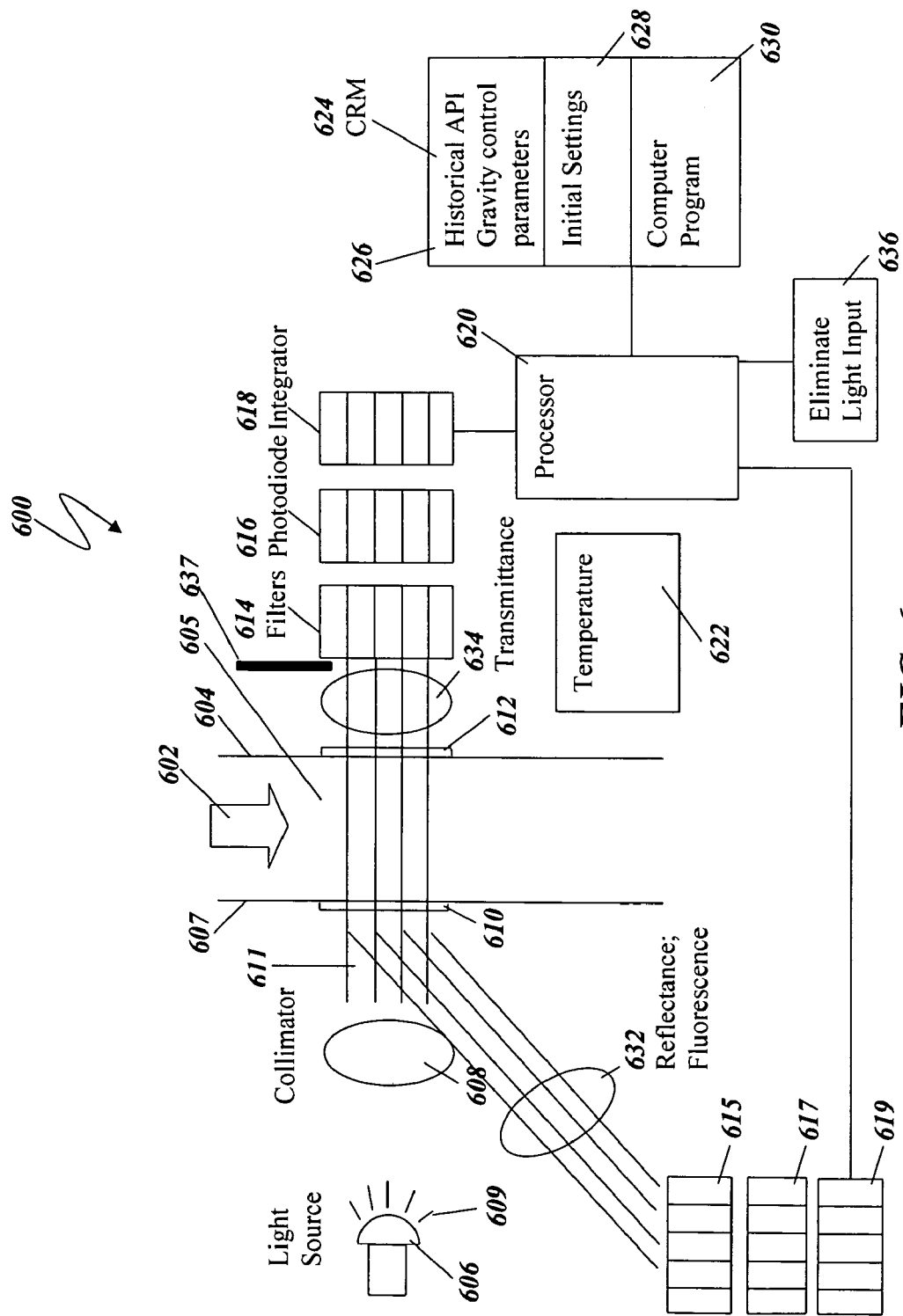
FIG. 6 is a schematic diagram of the integration circuit in an operational environment provided in another illustrative embodiment.

Turning now to FIG. 5 in another particular embodiment a light integration circuit 200 is provided for each wavelength of light passed by a filter as shown in FIG. 6. The integration circuit 200 measures the integrated photo current 214 $V_0$ of a photodiode 210 PD1 output current signal with noise, disturbances or an erratic pulse height, cycle and/or width. Light integration is started by opening switch 208 for an integration time. An integration circuit amplifier 212 accumulates the photocurrent generated in each wavelength by each a photodiode in an integration capacitance, C1 202 (also referred to herein as an integrating capacitor) as shown in FIG. 5. By measuring the output voltage, $V_0$ 214 simultaneously with light integration start 206, the average output current $I_{SC}$ can be obtained from the integration time, t and the capacitance C1. The capacitor C1 should feature low self-discharge to minimize errors. In another embodiment, the switch is an electronic analog switch. The integration time t is chosen and adjusted by means of a digital closed-loop control. In another embodiment, the digital closed-loop control is a processor based PID-type closed loop control. In another embodiment, a processor performs the integration of $I_{SC}$ by digitally processing a digitized representation of the output signal $I_{SC}$.

Each of the plurality of photodiodes provided in an illustrative embodiment is provided with a separate integration circuit so that each photodiode for each wavelength is measured and integrated separately. In another embodiment, noise on the photodiode output current is averaged out by the integration circuit. In another embodiment the integration is performed digitally by a processor shown in FIG. 6 for each wavelength.

Turning now to FIG. 6, in another illustrative embodiment 600 fluid 602 flows in a fluid channel 605 defined by fluid passage walls 604 and 607. The fluid passage may be associated with a sample tank. As fluid 602 flows through the fluid passage 605 it is exposed to light from the light source 606. Light source 606 emits light 609 which is collimated by a collimator 608. In another embodiment the light source is an ultraviolet source. In another embodiment the light is broadband white light. In another embodiment the light is infrared light. In another embodiment the light is near infrared light. In another embodiment the light is mid-infrared light. In another embodiment the light 609 is not collimated. In either case, light 609 that passes through 634 the fluid 602 to the photodiodes 616 to measure transmittance or is reflected off 632 of the fluid 602 to the photodiodes 617. For fluorescence measurements, the fluorescent light 634 emitted by the fluid is passed to the photodiodes 616 through filters 614 to integrators 618. For reflectance or backscattering measurements, the reflected light 632 reflected by the fluid is passed to the photodiodes 617 through filters 615 to integrators 619.

For transmittance measurements, collimated light 611 or light 609 passes through sapphire window 610 and into fluid 602 in fluid passage 605. Light passes through fluid 602 and exits fluid passage 605 through second sapphire window 612. Light passing through fluid 602 through sapphire window 612 passes through filters 614 which divide the light into wavelengths. The light intensity in each wavelength is measured by photo diodes 616. A similar process and structure is used to measure reflected light 632 in each wavelength. Each set of filters 614, 615, photodiodes 616, 617 and integration circuits 618, 619 (as shown and described with respect to FIG. 5) form wavelength filter/photodiode/integration circuit set which enable a separate integrated intensity measurement for each filter center wavelength or frequency ban around the center wavelength, in transmittance, luminance or reflectance. The output of the photodiodes 616, 617 for each wavelength is integrated by one of the integrators in a set of integrators 618, 619 respectively. Thus each filter and photo diode and integrator is associated with a particular wavelength for the downhole optical analysis system. The combination of the filters photodiodes integrators can be used as a spectrometer for analyzing fluids downhole. In another embodiment, the processor performs digital integration by multiplexing and integrating the output of each photodiode in each wavelength.

As shown in FIG. 6, processor 620 is in data communication with integration circuits or integrators 618, 619 for controlling the integration time for each wavelength filter photodiode pair. In another embodiment, the processor is in multiplexed data communication with each of the photodiodes for performing digital integration of the photodiodes output for each wavelength. The processor 620 is also in data communication with the temperature reading device 622. Processor 620 is further in data communication with a computer readable medium 624. The processor can also eliminate light input by engaging switch 636 to turn off light source 606 or engage a shield 637 to block the input of the photo diodes from light input. A data structure is embedded in the computer readable medium 624. The data structure has a first field for holding data indicative of PID closed-loop control parameters 626 and a second field for holding data indicative of initial integration time settings 628 for each integrator for each wavelength integrator.

A computer program 630 is stored or embedded in the computer readable medium 624. The computer readable medium provides a functional and spatial interrelationship between the data and instructions stored in the computer readable medium and the processor. The computer program comprises instructions that when executed by a computer perform a function and method useful for optical downhole and analysis as described herein and in further detail in FIG. 8.

Processor 620 samples the output of the photodiodes at a noise sampling frequency in order to sense disturbances or noise in the measurement of photo diode current output. In another embodiment a disturbance is defined by disturbance parameters which define an abrupt change over a relatively short period of time. In another embodiment disturbance parameters can be defined as a 10% change over 1-second duration in an optical intensity measurement for a particular wavelength. The disturbance can be indicative of noise caused by inhomogeneous fluid passing through the light 609 passing through the fluid stream or by an electrical disturbance on a power supply providing power to the photodiodes and integration circuit. The disturbance parameters are programmable and can be changed or tuned to more abrupt or less abrupt changes. Disturbance parameters can be defined as more or less percentage change in intensity over more or less duration.

Figure 7:
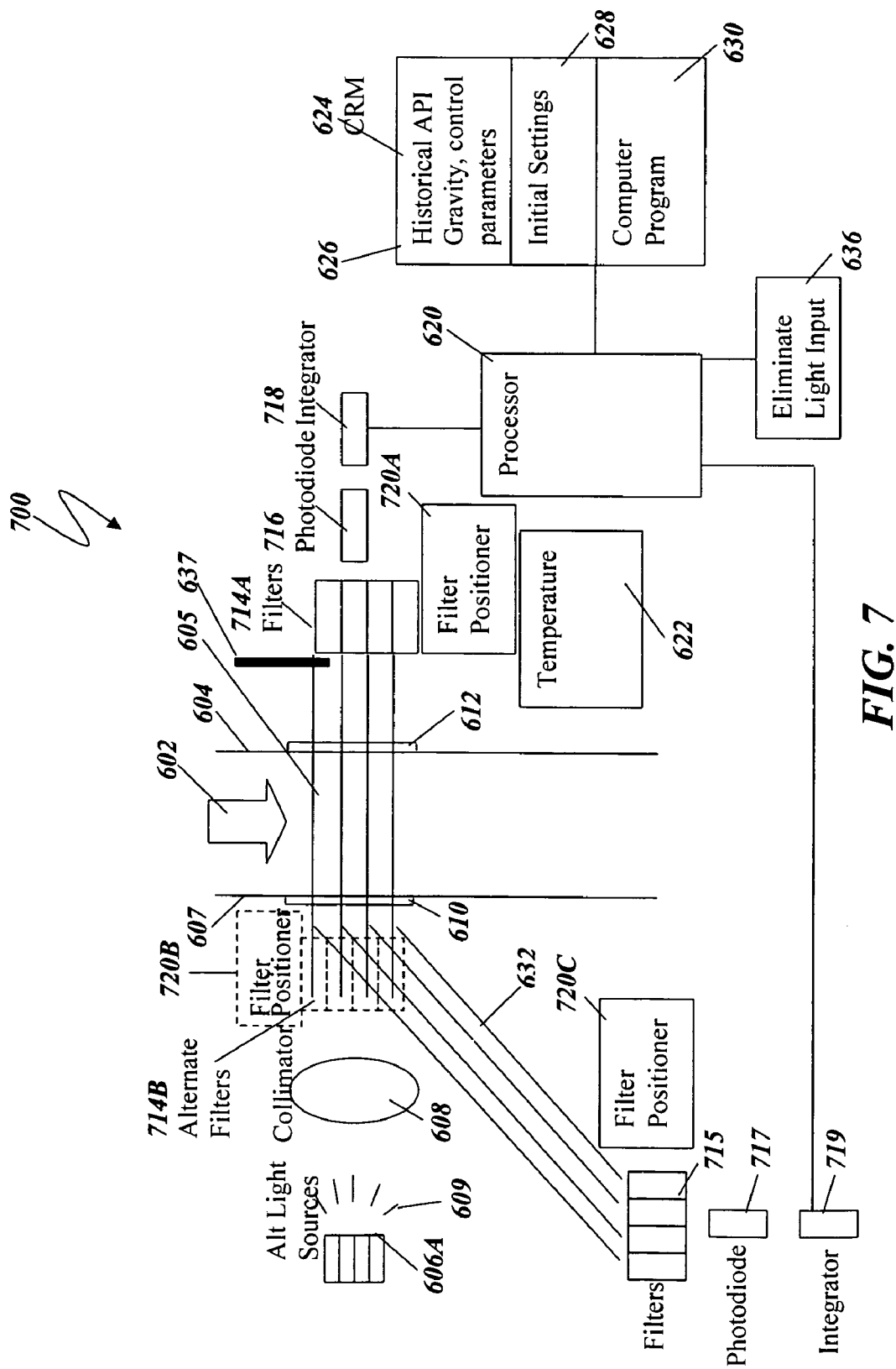
FIG. 7 is a schematic diagram of the integration circuit in an operational environment provided in another illustrative embodiment.

Turning now to FIG. 7, a single wavelength embodiment is shown in which one or more single wavelength filters 714A (post-filtering) or alternatively 714B (pre filtering) are positioned one at a time in optical alignment with single photodiode 716 by filter positioner 720A or 720B respectively. Single photodiode 716 and single integrator 718 measure transmitted light 634 at a single wavelength. As shown in FIG. 7, where a set of filters 714A or 714B are provided, each filter in a set of filters is positioned one at a time sequentially by a filter positioner so that a single wavelength associated with each filter is transmitted to photodiode 716 and measured/integrated sequentially. Similarly a single wavelength is passed sequentially by a set of single wavelength filters 715 and filter positioner 720C to photodiode 717 and single integrator 719 to measure reflected and fluorescent light 632. In another embodiment, a single filter can also be provided in place of the filter sets for pre or post filtering at a single wavelength. In another embodiment, a set of single wavelength light sources 606A are provided which are sequentially turned on by processor 620 to sequentially provide a single wavelength of light through the fluid from each single wavelength light source. In this embodiment, the filters can be eliminated as a single wavelength of light is transmitted, thus filtering may not be desired, however, the filters can be included if filtering is desired.

Figure 8:
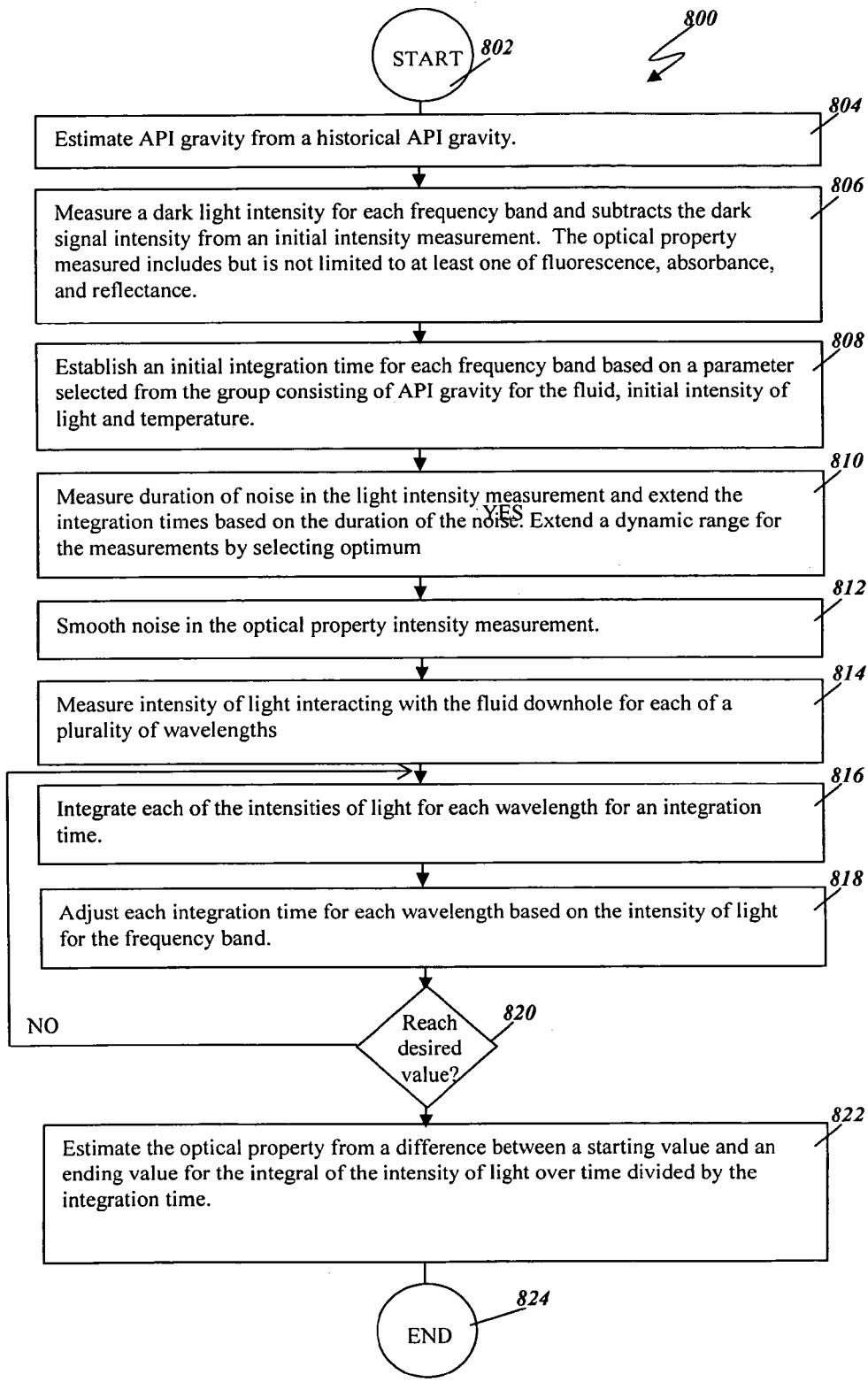
FIG. 8 is a flowchart showing functions performed in another illustrative embodiment.

Turning now to FIG. 8, a flow chart of functions performed in another embodiment of an apparatus and method is depicted. FIG. 8 is not intended to mandate any particular sequence of functions performed. Any one or more of the functions shown performed in blocks 804-822 can be left out or included in another particular embodiment. Each of the functions performed in blocks 804-822, if included in another particular embodiment, can be performed any order in the particular embodiment. As shown in FIG. 8, a method for measuring optical properties of a fluid downhole is disclosed.

The flowchart starts at block 802. At block 804 the apparatus and method estimate API gravity from a historical API gravity value.

At block 806 the apparatus and method measure an integrated dark light intensity for each frequency band or wavelength and subtracts the dark signal intensity from an initial intensity measurement. The dark current signal for each frequency band or wavelength uses the same integration time as the light intensity measurement for the corresponding wavelength or frequency band. The optical property measured includes but is not limited to at least one of fluorescence, absorbance, and reflectance. At block 808 the processor method establishes an initial integration time for each frequency band or wavelength measurement based on a parameter selected from the group consisting of API gravity for the fluid, initial intensity of light and temperature.

At block 810 the apparatus and method measure duration of noise in the light intensity measurement and extend the integration times based on the duration of the noise. In another illustrative embodiment, at block 812 the apparatus and method smooth noise in the optical property intensity measurement. In another illustrative embodiment at block 814 the apparatus and method measure intensities of light interacting with the fluid downhole for each of a plurality of wavelengths or frequency bands. At block 816 in another embodiment, the apparatus and method integrate each of the intensities of light for each frequency band for an integration time. At block 818 the processor and method adjusts each integration time for each wavelength based on the intensity of light for the wavelength. If no is the decision at decision block 820 the processor and method loop back and repeat block 816.

At decision block 820 the apparatus and method determine whether an integrated current desired value has been reached. In another embodiment a desired integrated current value for each wavelength is stored in the computer readable medium. In another embodiment a desired integrated current value for each wavelength is within the range of an analog to digital converter built into the processor. In another embodiment a desired integrated current value for each wavelength is below the maximum voltage rating for the analog to digital converter. In another embodiment a desired integrated current value for each wavelength is below a voltage rating for the capacitor. In another embodiment a desired integrated current value for each wavelength is 50% of the voltage rating of the analog to digital converter. In another embodiment a desired integrated current value for each wavelength is 80% of the voltage rating of the analog to digital converter. In another embodiment a desired integrated current value for each wavelength is 20% of the voltage rating of the analog to digital converter. The desired value is programmable and is set based on noise levels and temperature as a higher percentage voltage value may be used in the presence of high temperature to accommodate the higher noise levels associated with higher temperature.

If the desired valued has been reached, that is, "yes" is the decision at decision block 820, the processor and method go to block 822. At block 822, the processor and method estimate the optical property from a difference between a starting value and an ending value for the integral of the intensity of light over time divided by the integration time. Light intensity for each of the plurality of frequency bands is measured using a discrete photodiode. The apparatus and method flow chart ends at block 824.

The foregoing example is for purposes of example only and is not intended to limit the scope of the invention which is defined by the following claims. The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method for estimating an optical property of a fluid downhole, the method comprising:
   detecting light interacting with the fluid downhole;
   measuring an integral of the detected light with respect to time for an integration time; and
   estimating the optical property from a difference between a starting value and an ending value for the integral divided by the integration time.

2. The method of claim 1, wherein the measurement of light further comprises measurement of light for each of one or more wavelengths detected using a discrete photodiode, the method further comprising:
   adjusting the integration time for each wavelength based on an initial measurement of light for each wavelength.

3. The method of claim 1, the method further comprising:
   establishing an initial integration time based on a parameter selected from the group consisting of API gravity for the fluid, initial intensity of light and temperature.

4. The method of claim 3, wherein API gravity is estimated from historical API gravity data stored in a computer readable medium downhole.

5. The method of claim 1, the method further comprising:
   measuring an integrated dark light intensity; and
   subtracting the integrated dark signal intensity from an initial measurement of light.

6. The method of claim 1, wherein the optical property is a spectrum of light selected from the group consisting of fluorescence, absorbance, and reflectance.

7. The method of claim 1, wherein the fluid is selected from a group consisting of a gas, supercritical gas and mixture.

8. The method of claim 1, the method further comprising:
   sampling each measurement of light for noise at a noise sampling rate, wherein the noise sampling rate is faster than a sampling rate for the integrated measured light; and
   smoothing noise in the integrated measurement of light.

9. The method of claim 8, wherein the noise is caused by a source selected from the group consisting of photo diode, light source instability or an inhomogeneous fluid in the measurement chamber.

10. The method of claim 8, the method further comprising:
    measuring duration of the noise in the measurement of light;
    extending the integration time for each wavelength based on the duration of the noise; and
    eliminating a measurement for a wavelength when the duration of the noise for the wavelength is longer than the integration time for the wavelength.

11. The method of claim 1, the method further comprising:
    ending the integration time where the integrated measured of light has reached a value selected from the group consisting of a percentage of an analog to digital converter range and a voltage rating for an integrating capacitor.

12. An integrator circuit apparatus for estimating an optical property of a fluid downhole, the apparatus comprising: a discrete photo detector in optical communication with the fluid downhole an accumulator in electrical communication with an output of the photo detector; a processor in communication with the accumulator; and a computer readable medium, containing a computer program that when executed by the processor estimates the optical property from a difference between a starting value and an ending value for the accumulated output of the photo detector, divided by an integration time.

13. The apparatus of claim 12, the apparatus further comprising:
    a processor that estimates the optical property for a plurality of wavelengths from
    a difference between a starting value and an ending value for the accumulated output of the photo detector.

14. The apparatus of claim 13, the apparatus further comprising:
    one or more discrete photodiodes, wherein the wherein the photo detector output further comprises a measurement of light for each of wavelength is measured with one of the discrete photodiodes; and
    an integration time controller that adjusts each integration time for each wavelength based on the accumulated output of the photo detector for the wavelength.

15. The apparatus of claim 13, the integration time control further comprising an initial integration time value for each wavelength based on a parameter selected from the group consisting of API gravity for the fluid, initial intensity of light for the wavelength and downhole temperature.

16. The apparatus of claim 15, wherein API gravity for the fluid is estimated from a historical API gravity data stored in a computer readable medium.

17. The apparatus of claim 13, the apparatus further comprising;
- a light input control that substantially eliminates light entering the photodiodes for measuring dark signal intensity for each photodiode to subtract the dark signal intensity from the initial intensity measurement for the photo diodes.

18. The apparatus of claim 13, wherein the integration circuit ends the integration time for a wavelength when the accumulated output of the photo detector for the wavelength has reached a value selected from the group consisting of a predetermined percentage of a digital input range and an integrating capacitor voltage.

19. The apparatus of claim 12, wherein the optical property is a spectrum of the light selected from the group consisting of fluorescence, absorbance, and reflectance.

20. The apparatus of claim 12, wherein the fluid is selected from the group consisting of a gas, supercritical gas and a mixture.

21. The apparatus of claim 12, wherein the apparatus samples each measurement of light for noise at a noise sampling rate, wherein the noise sampling rate is faster than an sampling rate for the integrated measured intensity of light and smoothes noise in the measurement.

22. The apparatus of claim 12, wherein the noise is caused by a source selected from the group consisting of photo diode, light source instability or an inhomogeneous fluid in the measurement chamber.

23. The apparatus of claim 12, the apparatus further comprising:
- a circuit that measures duration of noise in the accumulated output of the photo detector; and
- a circuit that extends the integration time for at least one wavelength based on the duration of the noise and eliminates a measurement for a wavelength if the duration of noise is longer than the integration time for the wavelength.

24. The apparatus of claim 12, wherein the accumulator is integrated into the processor.

25. The apparatus of claim 12, wherein the accumulator is an analog device and the processor is a digital device.

26. The apparatus of claim 25, further comprising:
- an analog to digital converter positioned between the accumulator and the processor.

* * * * *